United States Patent
Gu

(10) Patent No.: US 11,930,755 B2
(45) Date of Patent: Mar. 19, 2024

(54) RICE VARIETY MM17

(71) Applicant: Missouri Rice Research and Merchandising Council, Bernie, MO (US)

(72) Inventor: Xingyou Gu, Brookings, SD (US)

(73) Assignee: Missouri Rice Research and Merchandising Council, Bernie, MO (US)

(*) Notice: Subject to any disclaimer, the term of this patent is extended or adjusted under 35 U.S.C. 154(b) by 0 days.

(21) Appl. No.: 17/206,970

(22) Filed: Mar. 19, 2021

(65) Prior Publication Data

US 2021/0289732 A1    Sep. 23, 2021

Related U.S. Application Data

(60) Provisional application No. 62/992,709, filed on Mar. 20, 2020.

(51) Int. Cl.
| | | |
|---|---|---|
| *A01H 6/46* | (2018.01) | |
| *A01H 4/00* | (2006.01) | |
| *A01H 5/10* | (2018.01) | |
| *A23L 7/196* | (2016.01) | |

(52) U.S. Cl.
CPC ........... *A01H 6/4636* (2018.05); *A01H 4/008* (2013.01); *A01H 5/10* (2013.01); *A23L 7/196* (2016.08)

(58) Field of Classification Search
CPC .................................................... A01H 6/4636
See application file for complete search history.

(56) References Cited

PUBLICATIONS

Specialists Speak, Ricefarming.com, Jan. 15, 2016, pp. 1-6 (Year: 2016).*

* cited by examiner

*Primary Examiner* — Brent T Page
(74) *Attorney, Agent, or Firm* — Stinson LLP

(57) ABSTRACT

The semi-dwarf, mid-season, medium grain rice variety MM17 is disclosed. The invention relates to the seeds and plants of the semi-dwarf, mid-season, medium grain rice variety MM17. The invention also relates to methods for producing a rice plant produced by crossing the semi-dwarf, mid-season, medium grain rice variety MM17 with itself or another variety.

10 Claims, 6 Drawing Sheets

RICE VARIETY MM17

CROSS REFERENCE TO RELATED APPLICATIONS

This application claims the benefit of U.S. Provisional Patent Application No. 62/992,709, filed Mar. 20, 2020. The entire contents of the above application are hereby incorporated by reference in its entirety.

BACKGROUND

The present disclosure is directed to a semi-dwarf, mid-season, medium grain rice variety named "MM17."

Rice is an important agricultural product and is one of the world's most prevalent food crops.

When undertaking breeding of rice plants (*Oryza sativa*), increasing yield is a primary objective. Other characteristics may also be desirable in the breeding of rice plants, such as a certain physical appearance of the plant or rice. For example, the color, shape, texture, etc. of the panicle, leaf blade, leaf sheath, or root of the rice plant. It also may be desirable to achieve a rice plant that exhibits certain processability properties, such as the milling quality of the rice.

Accordingly, a need exists for new and improved rice plants that exhibit desirable traits, including visual appearance, crop yield, and milling quality.

BRIEF SUMMARY

The present disclosure is directed to a seed of rice variety "MM17."

The present disclosure is also directed to a rice plant grown from the seed of rice variety MM17. For example, the rice plant grown from the seed of rice variety MM17 may comprise an average straight length of from about 3 mm to about 6 mm; an average length to width ratio (L/W) of from about 1.5 to about 2.5; and average amylose content of about 12% or less.

The present disclosure is further directed to a rice plant, or part thereof, having all the physiological and morphological characteristics of the inbred variety MM17.

The present disclosure is further directed to a rice plant regenerated from a tissue culture of a rice plant, or a part thereof, produced by growing the seed of rice variety MM17, wherein the plant has all the morphological and physiological characteristics of variety MM17.

Other objects and features will be in part apparent and in part pointed out hereinafter.

DETAILED DESCRIPTION

Figure 1A:
FIGS. 1a and 1b show an elevated growing box containing the *Oryza sativa* MM17 plant.
Figure 1B:
Figure 2A:
FIGS. 2a through 2c show a rice paddy containing the *Oryza sativa* MM17 plant.
Figure 2B:
Figure 2C:

The present disclosure relates to a new and distinct variety of medium grain rice (*Oryza sativa*). The variety is designated by the cultivar name "MM17."

Rice is the seed of the monocot plant *Oryza sativa*. Mature *Oryza sativa* plants are typically between 37 and 42 inches tall. *Oryza sativa* is native to Asia and is commonly referred to as "Asian rice."

The plant can be grown under mid-south growing conditions, typically from April to August. Mid-south conditions average about 60 inches of rain per year, with most of the rain falling in the spring. The summer typically entails high temperatures and dry conditions.

The leaves of the rice plant *Oryza sativa* are smooth and dark green in color. Leaf culms, leaf blades and flag leaves are erect. The lemma and palea of the plant are typically straw-colored and glabrous.

The grain is separated from the stalk of the *Oryza sativa* plant and the grains are dried and milled to prepare the rice.

The new MM17 rice variety is the result of a modified pedigree selection made by the inventor at a farm in Glennonville, Mo., which was a cross between a short grain rice variety developed in Italy—BALDO, and an experimental line from the Cooperative Uniform Regional Rice Nurseries (URRN)—RU00201093 (LBNT/9902/3/DAWN/9695//STBN/4/LGRU/5/WLLS). The inventor observed a cross between BALDO and RU00201093 to prepare the variant set forth in certificate of plant variety protection PVPO No. 201500336 (hereinafter referenced as "MM14"). The MM17 variant of the present disclosure was selected and purified from the MM14 variant by pedigree selection. The MM17 variant is a semi-dwarf, mid-season, medium grain rice.

Approximately 1,500 single panicles were selected from a plot containing a *Oryza sativa* cross between a short grain rice variety BALDO and an experimental line from the Cooperative Uniform Regional Rice Nurseries (URRN) (MM14)

Panicle lines were generated from the selected panicles in a winter nursery to increase the seeds and remove off-type plants from individual lines.

The selected panicles were then planted in plots located at The University of Puerto Rico in Puerto Rico.

Rice was grown and the MM17 rice variety was selected from the resulting plants.

The medium grain rice variety MM17 of the present disclosure is an improvement over the previously known species in that it exhibits columnar growth habit; smooth and dark green color leaves; and erect leaf culms, leaf blades, and flag leaves. The new MM17 rice variety is expected to perform as well as the species varieties.

In various embodiments, the *Oryza sativa* plant grown from the seed of rice variety MM17 of the present disclosure exhibits leaves that are smooth and dark green in color. The leaf culms, leaf blades, and flag leaves are erect.

In certain embodiments, the *Oryza sativa* plant grown from the seed of rice variety MM17 the present disclosure has no pests or diseases known to the inventor.

In some embodiments, the *Oryza sativa* plant grown from the seed of rice variety MM17 of the present disclosure has been observed to tolerate high temperatures of about 95° F. and low temperatures of about 10° F. when grown in USDA Plant Hardiness Zones 5b through 7b. In certain embodiments, the new *Oryza sativa* MM17 variety is generally suitable for growing in USDA Plant Hardiness Zones 5b through 10a. For example, the new *Oryza sativa* MM17 variety is generally suitable for the conditions present in states such as Missouri, Arkansas, Louisiana, Texas, and Mississippi.

In various embodiments, the *Oryza sativa* plant grown from the seed of rice variety MM17 of the present disclosure exhibits 50% heading at approximately 90 days from emergence. For example, at about 105 or less, at about 100 or less, at about 95 or less, at about 94 or less, at about 93 or less, at about 92 or less, at about 91 or less, at about 90 or less, at about 89 or less, at about 88 or less, at about 87 or less, at about 86 or less, or at about 85 or less days.

In certain embodiments, the *Oryza sativa* plant grown from the seed of rice variety MM17 of the present disclosure exhibited certain desirable disease ratings on a scale of 0 to 9.

In one embodiment, the sheath blight is about 7 or less, about 6 or less, about 5 or less, or about 4 or less. For example, in one embodiment, the sheath blight is about 5.4. In another embodiment, the sheath blight is about 5.7.

In another embodiment, the leaf blast is about 8 or less, about 7.5 or less, about 7 or less, about 6 or less, about 5 or less, about 4 or less, about 4.5 or less, or about 4 or less. For example, in one embodiment, the leaf blast is about 6.8. In another embodiment, the leaf blast is about 4.2.

In certain embodiments, the rotten neck blast was about 7 or less, about 6 or less, about 5 or less, about 4 or less, about 3 or less, or about 2 or less. For example, in one embodiment, the rotten neck blast is about 2.4. In another embodiment, the rotten neck blast is about 2.7.

In one embodiment, the bacterial panicle blight is about 8 or less, about 7.5 or less, about 7 or less, about 6.5 or less, about 6 or less, about 5.5 or less, or about 5 or less. For example, in one embodiment, the bacterial panicle blight is about 6. In another embodiment, the bacterial panicle blight is about 5.5.

The characteristics of MM17 rice variety distinguish it from other typical medium grain rice variety and the known cultivars. At the time this medium grain rice variety was selected, MM17 was observed as an about 34 inch high plant exhibiting a columnar growth habit; smooth and dark green color leaves; and erect leaf culms, leaf blades, and flag leaves. Exemplary figures of the *Oryza sativa* plant grown from the seed of rice variety MM17 of the present disclosure are presented in FIGS. 1a through 2c at various stages of growth. The height of the rice plants was observed to be between about 34 and about 39 inches. Certain rice plants exhibited a height of about 38.5 inches.

In one embodiment, the *Oryza sativa* plant grown from the seed of rice variety MM17 of the present disclosure exhibits an average yield (bushels/acre) of about 150 or greater, about 160 or greater, about 170 or greater, about 180 or greater, about 190 or greater, or about 200 or greater. For example, in one embodiment, the average yield (bushels/acre) is about 180. In another embodiment, the average yield (bushels/acre) is about 200.

In another embodiment, the rice variety MM17 of the present disclosure exhibits a milling quality (average percent whole/total grain) of about 70/74. In a further embodiment, the milling quality is about 69/74.

In certain embodiments, the average percentage chalk in the milled rice variety MM17 is from about 1% to about 10%, from about 1% to about 9%, from about 1% to about 8%, from about 1% to about 7%, from about 1% to about 6%, from about 1% to about 5%, from about 1% to about 4%, from about 1% to about 3%, or from about 2% to about 3%. In one embodiment, the average percentage chalk in the milled rice variety MM17 is about 2.40%. In another embodiment, the average percentage chalk in the milled rice variety MM17 is about 6.25%.

In some embodiments, the head rice or percentage of milled rice with a length greater or equal to three quarters of the average length of the whole kernel is at least about 50%, at least about 60%, or at least about 70%. In one embodiment, the head rice is 70%. In another embodiment, the head rice is 69%.

In other embodiments, the total rice (also known as the milled rice yield) is at least about 50%, at least about 60%, or at least about 70%. In one embodiment, the total rice is 74%.

Figure 3:
FIG. 3 shows MM17 rice as recovered from the rice paddy.
Figure 4:
FIG. 4 shows milled MM17 rice.

Exemplary figures of the paddy rice and milled rice of the MM17 rice variety of the present disclosure are set forth in FIGS. 3 and 4.

In various embodiments, the average straight length of the MM17 rice variety is from about 3 mm to about 6 mm, from about 3.5 mm to about 6 mm, from about 4 mm to about 6 mm, from about 5 mm to about 6 mm, from about 5 mm to about 5.9 mm, from about 5 mm to about 5.8 mm, from about 5 mm to about 5.7 mm, from about 5 mm to about 5.6 mm, from about 5 mm to about 5.5 mm, from about 5.1 mm to about 5.5 mm, or from about 5.2 mm to about 5.4 mm. In one embodiment, the average straight length of the MM17 rice variety is about 5.33 mm. In another embodiment, the average straight length of the MM17 rice variety is about 5.7 mm.

In certain embodiments, the average straight width of the MM17 rice variety is from about 1 mm to about 5 mm, from about 2 mm to about 5 mm, from about 2 mm to about 4 mm, from about 2 mm to about 3 mm, or from about 2.25 mm to about 2.75 mm. In one embodiment, the average straight width of the MM17 rice variety is about 2.58 mm. In another embodiment, the average straight width of the MM17 rice variety is about 2.87 mm.

In some embodiments, the average length to width ratio (L/W) of the MM17 rice variety is from about 1.5 to about 2.5, from about 1.75 to about 2.5, from about 1.75 to about 2.25, from about 1.75 to about 2. In one embodiment, the average length to width ratio (L/W) of the MM17 rice variety is about 2.07. In another embodiment, the average length to width ratio (L/W) of the MM17 rice variety is about 2.0.

The MM17 rice variety is believed to be particularly useful as a cuisine product, including sushi-type cuisines. That is, the rice kernel produced from the MM17 rice plant may be used in preparing a food product. In certain embodiments, the rice kernel produced from the MM17 rice plant may be used in preparing a food product including sushi, sake, rice vinegar, rice syrup, rice milk, rice noodles, rice bread, and rice crackers. In one embodiment, the food product is sushi.

The MM17 rice variety has a short grain with a low amylose content and low gelatinization temperature. The MM17 rice variety is also non-aromatic.

In certain embodiments, the average amylose content of MM17 rice variety is about 12% or less, about 11% or less, about 10% or less, about 9% or less, about 8% or less, about 7% or less, or about 6% or less.

In one embodiment, the average amylose content of MM17 rice variety is 8.95%. This represents a clear improvement over the previously known varieties, for example the 'Jupiter' variety that has an average amylose content of 13.58%.

In certain other embodiments, the MM17 rice variety of the present disclosure exhibits an average alkali spreading value (ASV) of approximately 6. Therefore, in some embodiments, the MM17 rice variety exhibits a low gelatinization temperature.

MM17 will benefit growers who will profit from the desired yield, appearance, and low amylose content of the MM17 rice variety.

Desirable characteristics are glabrous, medium height, medium grain type, light brown pericarp, and/or brown hull fertile panicles with grain length to width ratio of about 2.0 mm.

MM17 has not been observed under all growing conditions, and variations may occur as a result of different growing conditions. Variants observed were pubescent, taller, shorter, later, earlier, short- and intermediate-grain types, gold and black hull, purple/discolored pericarp, and sterile panicle. Variations in grain dimension may occur as longer, shorter, thicker, or thinner grains. The total number of variants was less than 1 per 5,000.

In certain embodiments, the MM17 rice variety is moderately susceptible to sheath blight, blast, and bacterial panicle blight.

All progeny of MM17, insofar as have been observed by the inventor, have remained genetically stable in all characteristics described hereinafter. Other than as set out hereinafter, as of this time, no other characteristics have been observed by the inventor that are different from common *Oryza sativa* plants.

Having described the invention in detail, it will be apparent that modifications and variations are possible without departing from the scope of the invention defined in the appended claims.

EXAMPLES

The following non-limiting examples are provided to further illustrate the MM17 rice variety.

Example 1

The MM17 rice variant was grown at Glennonville, Mo. and evaluated for disease rating and grain quality traits.

The results are set forth below in Tables 1-3. The disease scores are reported on a scale of 0 to 9, with 0 representing a disease resistant crop and 9 representing crop very susceptible to disease.

TABLE 1

| | |
|---|---|
| Yield (bushels/acre) | 181 |
| Head Rice (%) | 70 |
| Total Rice (%) | 74 |
| Height (in) | 34 |
| Days to 50% Heading | 90 |
| Lodging (%) | 1 |

TABLE 2

| | |
|---|---|
| Sheath Blight (0-9) | 5.4 |
| Leaf Blast (0-9) | 6.8 |
| Rotten Neck Blast (0-9) | 2.4 |
| Bacterial Panicle Blight (0-9) | 6 |

TABLE 3

| | |
|---|---|
| Amylose Content (%) | 8.9 |
| Gel Temperature (1-7) | 6 |
| Average Straight Length (mm) | 5.33 |
| Average Straight Width (mm) | 2.58 |
| Average L/W Ratio | 2.07 |
| Average % Chalk in Milled Rice | 2.40 |
| % Kernel with 0-5% Chalk | 91 |
| % Kernel with 5-10% Chalk | 4 |
| % Kernel with 10-30% Chalk | 2 |
| % Kernel with >30% Chalk | 1 |

Example 2

A series of further experiments were conducted on the MM17 rice variety. The rice plant was grown at three locations, referred to below as the "Rice Farm," "URRN" (Uniform Regional Rice Nursery)," and "Glenonnville" (Glenonnville, Mo.) locations. The results are reported below.

The disease scores are reported on a scale of 0 to 9, with 0 representing a disease resistant crop and 9 representing crop very susceptible to disease.

Rice Farm data is reported below in Tables 4-6.

TABLE 4

| Rice Farm - Agronomical Data | | | |
|---|---|---|---|
| Agronomic data | Year 1 | Year 2 | Year 3 |
| Yield (bushels/acre) | — | — | — |
| Heading date (days) | 103 | — | 97 |
| Total Rice (%) | 74 | — | 75 |
| Head Rice (%) | 65 | — | 45 |
| Height (cm) | 96 | — | 96 |
| Whiteness | 40.2 | — | — |
| Transparency | 2.6 | — | — |
| Polishness | 93.1 | — | — |
| Lodging (0-10) | 0 | — | — |

TABLE 5

| Rice Farm - Grain Dimension | | | |
|---|---|---|---|
| Grain dimension | Year 1 | Year 2 | Year 3 |
| Length (mm) | — | 5.73 | 5.74 |
| Width (mm) | — | 2.85 | 2.905 |
| L/W ratio | — | 2.01 | 1.98 |
| % chalk | — | 7 | 5.5 |

TABLE 6

| Rice Farm - Disease Score | | | |
|---|---|---|---|
| Disease Score | Year 1 | Year 2 | Year 3 |
| Leaf Blast (0-9) | — | 2.5 | 6 |
| Rotten Neck Blast (0-9) | — | 3 | 2.5 |
| Sheath Blight (0-9) | — | 5.5 | 6 |
| Bacterial Panicle Blight (0-9) | — | 7 | 4 |

URRN data is reported below in Table 7.

TABLE 7

| URRN - Agronomic Data | | | |
|---|---|---|---|
| Agronomic data | Year 1 | Year 2 | Year 3 |
| Yield (bushels/acre) | — | — | — |
| Heading date (days) | — | 103 | 89 |
| Total Rice (%) | — | 72.3 | 74 |
| Head Rice (%) | — | 67.9 | 71 |
| Height (cm) | — | 97.8 | 101.3 |
| Whiteness | — | 40.2 | — |
| Transparency | — | 2.7 | — |
| Polishness | — | 95.5 | — |
| Lodging (0-10) | — | 0 | 0 |

Glenonnville data is reported below in Table 8.

TABLE 8

Glenonnville - Agronomic Data

| Agronomic data | Year 1 | Year 2 | Year 3 | Year 4 |
|---|---|---|---|---|
| Yield (bushels/acre) | — | — | — | — |
| Heading date (days) | — | — | — | — |
| Total Rice (%) | 73.7 | — | 74.4 | 75.7 |
| Head Rice (%) | 68.4 | — | 69.3 | 69.9 |
| Height (cm) | — | — | — | — |
| Whiteness | 41.5 | — | — | — |
| Transparency | 2.87 | — | — | — |
| Polishness | 102 | — | — | — |
| Lodging (0-10) | 0 | 0 | 0 | 0 |

The average values observed across all trials and across all years for the MM17 rice variant is set forth below in Tables 9-11.

TABLE 9

Agronomic Data

| Agronomic data | Average |
|---|---|
| Yield (bu/ac) | 200 |
| Heading date (days) | 98 |
| Total Rice (%) | 74 |
| Head Rice (%) | 65 |
| Height (cm) | 98 |
| Whiteness | 41 |
| Transparency | 2.7 |
| Polishness | 97 |
| Lodging (0-10) | 0 |

TABLE 10

Grain Dimension

| Grain dimension | Average |
|---|---|
| Length (mm) | 5.735 |
| Width (mm) | 2.8775 |
| L/W ratio | 1.995 |
| % chalk | 6.25 |

TABLE 11

Disease Score

| Disease Score | Average | Description |
|---|---|---|
| Leaf Blast (0-9) | 4.25 | moderately susceptible |
| Rotten Neck Blast (0-9) | 2.75 | moderately resistant |
| Sheath Blight (0-9) | 5.75 | susceptible |
| Bacterial Panicle Blight (0-9) | 5.5 | susceptible |

Example 3

A further MM17 rice variant was tested and exhibited the following conditions.

TABLE 12

| Amylose Content (%) | 8.9 |
|---|---|
| Alkali spreading value (1-7) | 6 |
| Average Straight Length (mm) | 5.73 |

TABLE 12-continued

| Average Straight Width (mm) | 2.88 |
|---|---|
| Average L/W Ratio | 2.0 |
| Average % Chalk in Milled Rice | 6.25 |
| % Kernel with 0-5% Chalk | 91 |
| % Kernel with 5-10% Chalk | 4 |

Example 4

In a further experiment, the characteristics of the MM17 rice variety was tested as compared to the Jupiter, Caffey, and CL271 varieties as shown below in Table 13.

TABLE 13

|  | MM17 | Jupiter | Caffey | CL271 |
|---|---|---|---|---|
| Rice Plant Height (in) | 34 | 36 | 36 | 35 |
| Average Amylose Content | 8.95% | 13.58% | — | — |
| Average Alkali Spreading Value (ASV) | 6 | ~6 |  |  |
| Milling Quality (average percent whole/total grain) | 70/74 | 67/74 | 64/73 | 68/74 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

DEPOSIT INFORMATION

Rice Designated "MM17"

A deposit of the rice designated "MM17" consisting of 25 packets containing 25 seeds was made with the American Type Culture Collection, ATCC®), ATCC® Patent Depository, 10801 University Boulevard, Manassas, Va., 20110, USA, and assigned ATCC® Accession Number PTA-127706. The date of deposit was Jan. 8, 2024. The deposit is intended by Applicant to meet all of the requirements of 37 C.F.R. §§ 1.801-1.809.

The invention claimed is:

1. A rice plant designated as "MM17" comprising:
   a height ranging from about 34 inches to about 39 inches;
   a columnar growth habit;
   a smooth and dark green leaf color;
   erect leaf culms;
   erect leaf blades; and
   erect flag leaves;
   when grown in USDA Plant Hardiness Zones 5b through 10a; and
   wherein a rice kernel from the rice plant comprises: an average straight length of from about 3 mm to about 6 mm;
   an average length to width ratio (L/W) of from about 1.5 to about 2.5; and
   average amylose content of about 12% or less; and
   representative sample of the rice plant having been deposited under ATCC® Accession Number PTA-127706.

2. A tissue culture of cells produced from the rice plant of claim 1, wherein said cells of the tissue culture are produced from a plant part selected from the group consisting of leaves, pollen, embryos, cotyledon, hypocotyl, meristematic cells, roots, root tips, pistils, anthers, flowers, stems, glumes and panicles.

3. A rice plant regenerated from the tissue culture of claim 2, wherein the plant has all the morphological and physiological characteristics of the rice plant designated as MM17.

4. A rice seed produced from the rice plant of claim 1.

5. A rice seed produced from the rice plant of claim 3.

6. A rice kernel produced from the rice plant of claim 1, the rice kernel comprising: an average straight length of from about 3 mm to about 6 mm; an average length to width ratio (L/W) of from about 1.5 to about 2.5; and average amylose content of about 12% or less.

7. A rice kernel produced from the rice plant of claim 3, the rice kernel comprising: an average straight length of from about 3 mm to about 6 mm; an average length to width ratio (L/W) of from about 1.5 to about 2.5; and average amylose content of about 12% or less.

8. A food product prepared with a rice kernel produced from the rice plant designated as "MM17" according to claim 1.

9. The food product of claim 8, wherein the food product is selected from the group consisting of sushi, sake, rice vinegar, rice syrup, rice milk, rice noodles, rice bread, and rice crackers.

10. The food product of claim 8, wherein the food product is sushi.

* * * * *